United States Patent
Zhang et al.

(10) Patent No.: US 9,288,984 B2
(45) Date of Patent: Mar. 22, 2016

(54) HERBICIDAL CONCENTRATE COMPOSITIONS CONTAINING GLYPHOSATE AND DICAMBA SALTS

(75) Inventors: Hong Zhang, Carmel, IN (US); Holger Tank, Zionsville, IN (US); Mei Li, Westfield, IN (US); Lei Liu, Carmel, IN (US); Stephen L. Wilson, Zionsville, IN (US); Kuide Qin, Westfield, IN (US); David G. Ouse, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 604 days.

(21) Appl. No.: 12/822,373

(22) Filed: Jun. 24, 2010

(65) Prior Publication Data

US 2010/0331182 A1     Dec. 30, 2010

Related U.S. Application Data

(60) Provisional application No. 61/220,332, filed on Jun. 25, 2009, provisional application No. 61/255,649, filed on Oct. 28, 2009.

(51) Int. Cl.
*A01N 37/40* (2006.01)
*A01N 57/20* (2006.01)

(52) U.S. Cl.
CPC .............. *A01N 37/40* (2013.01); *A01N 57/20* (2013.01)

(58) Field of Classification Search
None
See application file for complete search history.

(56) References Cited

U.S. PATENT DOCUMENTS

| 5,175,353 | A  | * | 12/1992 | Jones et al. | 562/474 |
| 5,965,487 | A  | * | 10/1999 | Flahive | 504/130 |
| 6,831,038 | B2 | * | 12/2004 | Volgas et al. | 504/206 |
| 2001/0019997 | A1 | * | 9/2001 | Wright | 504/206 |
| 2003/0060370 | A1 | * | 3/2003 | Jones | 504/206 |
| 2006/0019828 | A1 | * | 1/2006 | Becher et al. | 504/116.1 |
| 2012/0115816 | A1 | * | 5/2012 | Ramsay et al. | 514/114 |
| 2012/0142532 | A1 | * | 6/2012 | Wright | A01N 25/32 504/144 |

FOREIGN PATENT DOCUMENTS

| WO | WO 2008030749 A2 * | 3/2008 | A01N 25/02 |
| WO | WO2010/102102 A1 | 9/2010 | |
| WO | WO 2010151622 | 12/2010 | |

OTHER PUBLICATIONS

Micro Flo BANVEL Specimen Label, Sep. 13, 2004.*
Glyphosate WHO monograph No. 159 (1994).*
Morales Letter (1995), [Downloaded on Sep. 25, 2014 from the website http://www.epa.gov/pesticides/chem_search/cleared_reviews/csr_PC-103601_29-Jun-95_281.pdf].*
Micro Flo: "Banvel Herbicide", Specimen Label, Sep. 13, 2004, pp. 1-12, xp002624757, Retrieved from the Internet: URL: http://www.golfenviro.com/ftp/BanvelLabel.pdf [retrieved on Feb. 23, 2011].

* cited by examiner

*Primary Examiner* — Robert A Wax
*Assistant Examiner* — Thor Nielsen
(74) *Attorney, Agent, or Firm* — Michael J. Terapane

(57) ABSTRACT

The mixture of potassium or certain amine salts of glyphosate and dicamba allows the preparation of high-strength liquid compositions containing greater than 300 gae/L of total active ingredient loading if the pH is adjusted between about 6.0 and about 8.0. Compositions are particularly well-suited for herbicidal applications on crops that are resistant or tolerant to both glyphosate and dicamba.

21 Claims, No Drawings

HERBICIDAL CONCENTRATE COMPOSITIONS CONTAINING GLYPHOSATE AND DICAMBA SALTS

This application claims the benefit of U.S. Provisional Applications Ser. No. 61/220,332 filed on 25 Jun. 2009 and 61/255,649 filed on 28 Oct. 2009. The present invention relates to herbicidal compositions containing salts of N-(phosphono-methyl)glycine (glyphosate) and 3,6-dichloro-2-methoxybenzoic acid (dicamba).

FIELD OF THE INVENTION

Background of the Invention

Glyphosate and dicamba are known, effective herbicides. Various formulations are currently marketed, many of which are aqueous solutions that can be used as is or diluted prior to use. Typically both the glyphosate and the dicamba are provided as salts, which exhibit sufficiently high solubility in water to provide a high-strength herbicidal formulation. Premix formulations of glyphosate isopropylamine (IPA) salt and dicamba IPA salt are known in the industry and typically used for the control or suppression of emerged weeds in fallow and reduced tillage systems. However, the total active ingredient loading (grams acid equivalent per liter [gae/L] glyphosate IPA+gae/L dicamba IPA) in the commercially available formulations is limited to less than 300 gae/L if the ratio of glyphosate (gae/L) to dicamba (gae/L) is between the desired ratios of 1:1 to 3:1. A higher-strength formulation is desirable for a variety of economic and environmental reasons. For example, it is desirable to provide a high-strength formulation to reduce shipping and handling costs and to reduce the amount of packaging material that must be disposed. The high-strength formulations should be stable and retain potency during storage and shipping. Furthermore, the high-strength formulation should be a homogeneous liquid that is stable at temperatures at least as high as 50° C. and should not exhibit any precipitation or phase separation at temperatures at least as low as 0° C.

SUMMARY OF THE INVENTION

It has now been found that the mixture of potassium or certain amine salts of glyphosate and dicamba allows the preparation of high-strength liquid compositions containing up to or greater than 450 gae/L of total active ingredient loading if the pH is adjusted to about 6.0 to about 8.0. The present invention provides a homogeneous, stable, high-strength aqueous herbicidal concentrate composition comprising:
 (a) water,
 (b) a glyphosate potassium or amine salt, and
 (c) a dicamba potassium or amine salt,
in which (i) the glyphosate salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (ii) the dicamba salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (iii) the composition contains a total active ingredient loading of at least 300 gae/L of the glyphosate salt and the dicamba salt, (iv) the acid equivalent weight ratio of the glyphosate salt in grams acid equivalent per liter (gae/L) to the dicamba salt in gae/L is from about 1:1 to about 3:1, and (v) the pH is from about 6.0 to about 8.0. Furthermore, one or more cosolvents and/or efficacy-enhancing surfactants can optionally be incorporated into the high-strength composition while still maintaining the high loading. Optionally, a second auxin type herbicide can be incorporated in the composition. Auxin type herbicides include chlorophenoxy acids such as 2,4-dichlorophenoxy acetic acid [2,4-D], 2,4-dichlorophenoxy butyric acid [2,4-DB], (4-chloro-2-methylphenoxy)acetic acid [MCPA] and 4-(4-chloro-2-methylphenoxy)butanoic acid [MCPB]; pyridine carboxylic acids such as picloram, aminopyralid, fluoroxypyr, clopyralid and triclopyr; and quinoline carboxylic acids such as quinmerac and quinclorac.

In still yet another form, the present invention provides a method of treating plants with the herbicidal composition. The composition is typically applied as a post-emergent herbicide. While the composition can be applied as a highly concentrated solution, it is preferably diluted with water prior to application to the plants. While the composition can be used in a burn-down situation, it is particularly well-suited for application to crops that are resistant or tolerant to both glyphosate and dicamba.

DETAILED DESCRIPTION OF THE INVENTION

In general the present invention is directed to a homogeneous, stable, high-strength aqueous herbicidal concentrate composition containing a mixture of potassium or amine salts of glyphosate with potassium or amine salts of dicamba. More specifically, the present invention provides a high-strength aqueous herbicidal concentrate composition comprising:
 (a) water,
 (b) a glyphosate potassium or amine salt
 (c) a dicamba potassium or amine salt,
in which (i) the glyphosate salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (ii) the dicamba salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (iii) the composition contains a total active ingredient loading of at least 300 gae/L of the glyphosate amine salt or potassium salt and the dicamba amine salt or potassium salt, (iv) the acid equivalent weight ratio of the glyphosate salt to the dicamba salt is from about 1:1 to about 3:1, and (v) the pH is from about 6.0 to about 8.0.

The salts of glyphosate of the present invention may be potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually. Examples of preferred amine salts include monoethanolamine, dimethylethanolamine, dimethylamine, diglycolamine [2-(2-aminoethoxy)ethanol] or choline (2-hydroxyethyltrimethylammonium) salts. The salts of dicamba of the present invention may be potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from C₁-C₄ carbon atoms individually. Examples of preferred amine salts include dimethylamine, monoethanolamine, dimethylethanolamine, choline or diglycolamine [2-(2-aminoethoxy)-ethanol] salts. The amine salts of glyphosate and dicamba can either be the same or different.

The herbicidal composition includes the glyphosate potassium or amine salt and the dicamba potassium or amine salt in an amount sufficient to provide the high-strength composition. In preferred embodiments, the high-strength herbicidal composition includes a total active ingredient loading greater than about 300 gae/L based on the total glyphosate salt and dicamba salt; preferably, the high-strength herbicidal composition includes greater than about 400 gae/L based on the total glyphosate salt and dicamba salt; more preferably, the high-strength herbicidal composition includes greater than about 450 gae/L based on the total glyphosate salt and dicamba salt; most preferably, the high-strength herbicidal composition includes greater than about 470 gae/L based on the total glyphosate salt and dicamba salt.

In the compositions of the present invention, the weight ratio of the glyphosate potassium or amine salt to the dicamba potassium or amine salt expressed as gae/L is from about 1:1 to about 3:1, more preferably from about 1.5:1 to about 3:1.

In preferred embodiments, the present invention includes a high-strength herbicidal composition that is storage stable at high temperatures. That is, the composition forms a homogeneous, stable solution that does not exhibit cloudiness under the storage conditions. More preferably, the compositions of the present invention are stable at temperatures greater than or equal to about 50° C.; most preferably, at a temperature equal to or greater than about 60° C.

Furthermore, the herbicidal composition also does not exhibit phase separation or precipitation (or crystallization) of any of the components at low temperatures. For example, the high-strength composition remains a solution at temperatures below about 0° C., more preferably at temperatures below about −10° C., and most preferably at temperatures below about −20° C.

To maintain such stability the pH of the composition of the present invention should be adjusted to from between about 6.0 to about 8.0. The preferred pH is from between about 6.5 to about 7.5. The pH of the composition of the present invention can be conveniently controlled by preparing the high-strength aqueous herbicidal concentrate composition by neutralizing the glyphosate and dicamba acids with aqueous solutions of KOH or of the appropriate amines and using a slight excess of KOH or of the appropriate amines to adjust the pH to the desired range.

The high-strength herbicidal composition may optionally include one or more cosolvent and/or an efficacy-enhancing amount of a surfactant or surfactant mixture. In such embodiments, the cosolvent and/or surfactant is selected to be compatible in solution with the high concentration composition. By use of the term "compatible" in the present application, it will be understood by those skilled in the art to include within its meaning that the resulting solution does not exhibit a phase separation or precipitation in the composition that can be initially observed as a cloudiness and which is typically determined at a specified temperature.

Cosolvents conventionally used in the art of formulation and which may also optionally be used in the present compositions are solvents which are totally miscible with water, particularly in the presence of electrolytes. Cosolvents particularly well-suited for use in the present invention are preferably alcohols and glycols containing free hydroxy groups and include methyl alcohol, ethyl alcohol, isopropyl alcohol, amyl alcohol, ethylene glycol, propylene glycol, glycerine, propylene glycol monomethyl ether and diethylene glycol monomethyl ether and the like. Cosolvents can also be polar organic solvents and include dimethyl sulfoxide, N,N-dimethylformamide, tetrahydrofuran, mixture of N,N-dimethyl capramide and N,N-dimethyl caprylamide or N-methylpyrrolidone and the like.

The cosolvent can be included in the herbicidal composition in a desired concentration. If a cosolvent is used, the herbicidal composition includes the cosolvent in amounts between about 20 g/L and about 200 g/L, more preferably in amounts between about 50 g/L and about 100 g/L.

Surfactants conventionally used in the art of formulation and which may also optionally be used in the present compositions are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Surfactants particularly well-suited for use in the present invention are preferably selected to include one or more of the following types of compounds: alkylamine surfactants having 8 to 22 carbon atoms, such as Armeen DMTD, and Duomeen TTM; alkoxylated alkylamine surfactants having 8 to 22 carbon atoms and a total of 1-20 alkylene oxide groups, available for example from Akzo Nobel as Ethomeen™ C/12, Ethomeen T/12, Ethomeen T/20, Ethoduomeen T/13, and Propomeen T/12 respectively; ethoxylated etheramine surfactants, such as Tomah E-14-2, Tomah E-14-5 and Tomah E-17-5 respectively; amine oxide or ethoxylated amine oxide surfactants, such as Aromox C/12 and Aromox DMC from Akzo Nobel, Ammonyx LO and Ammonyx CDO from Stepan, and Tomah AO-14-2 from Air Products; amidoamine surfactant, such as Adsee C80W from Akzo Nobel; quaternary ammonium surfactants, such as Akzo Nobel's Arquad T/50, Arquad APA-E, Duoquad T/50, Ethoquad™ C/12, Ethoquad 18/12 and Air Products' Tomah Q-14-2; amphoteric surfactants, such as Dehyton AB-30 from Cognis, Geronol™ CF/AR 30 from Rhodia, and Tego™ Betaine F 50 from Goldschmidt; alcohol ethoxylates, such as Tergitol™ 15S20; alcohol ethoxylate phosphate esters such as Geranol CF/AR from Rhodia; alkylpolyglycosides such as Akzo Nobel AG 6202 or AG 6210; or anionic ester derivatives of alkylpolyglycosides such as the Eucarol™ AGE surfactants.

The surfactant can be included in the herbicidal composition in a desired concentration. If surfactants are used, preferably the desired concentration is sufficient to enhance the herbicidal activity of the resulting composition over that observed with a comparable herbicidal composition without the surfactants. More preferably, the herbicidal composition includes the surfactant in amounts between about 20 g/L and about 200 g/L; most preferably in amounts between about 50 g/L and about 100 g/L.

Optionally, a second auxin type herbicide can be incorporated in the composition. Auxin type herbicides include chlorophenoxy acids such as 2,4-dichlorophenoxy acetic acid [2,4-D], 2,4-dichlorophenoxy butyric acid [2,4-DB], (4-chloro-2-methylphenoxy)acetic acid [MCPA] and 4-(4-chloro-2-methylphenoxy)butanoic acid [MCPB]; pyridine carboxylic acids such as picloram, aminopyralid, fluoroxypyr, clopyralid and triclopyr; and quinoline carboxylic acids such as quinmerac and quinclorac.

The compositions described herein can be applied to plants in an amount sufficient to induce an herbicidal effect. For example, a composition prepared according to the present invention can be applied as an aqueous solution to plants including the plants' leaves, stems, branches, flowers and/or fruit. The herbicidal composition can be applied in an herbicidally effective amount sufficient to inhibit plant growth or kill individual plants.

The agricultural compositions prepared according to the present invention are highly effective as an herbicide composition against a variety of weeds. The compositions of the present invention can be used as is or combined with other components including other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, wetting agents, spreading agents, drift control agents, dispersing agents, thickening agents, freeze point depressants, antimicrobial agents, crop oil, other biologically and/or agriculturally active components and the like. The concentrated agricultural compositions are typically diluted in water and then applied by conventional means well known to those in the art.

The concentrated agricultural compositions of the present invention are particularly well-suited for application to crops that are resistant or tolerant to both glyphosate and dicamba. They can, further, be used in conjunction with glufosinate, 2,4-D or imidazolinones on glufosinate-tolerant, 2,4-D-tolerant or imidazolinone-tolerant crops.

Example 1

Preparation of Glyphosate Salt Solutions 50-60 g glyphosate technical were mixed with water and reacted with 1.25 molar equivalents of amine aqueous solutions or potassium hydroxide aqueous solution to form a homogeneous clear solution at ambient temperature. The pH of the solution was then adjusted to a range of 6-8 (Table 1) using additional amine or potassium hydroxide. Water was added, if needed, to reach a concentration of glyphosate given in Table 1.

TABLE 1

| Sample ID | Salt Type | Glyphosate Acid Equivalent Content | | |
|---|---|---|---|---|
| | | (ae wt %) | (g ae/L) | pH |
| G-1-1 | Dimethylamine (DMA) | 41.4 | 505 | 7.2 |
| G-1-2 | Dimethylamine (DMA) | 43.8 | 538 | 7.2 |
| G-2-1 | Monoethanolamine (EA) | 42.1 | 548 | 7.7 |
| G-3-1 | Dimethylethanolamine (DMEA) | 42.0 | 517 | 7.2 |
| G-3-2 | Dimethylethanolamine (DMEA) | 39.9 | 503 | 7.0 |
| G-4-1 | Choline hydroxide (Choline) | 41.0 | 521 | 7.2 |

TABLE 1-continued

| Sample ID | Salt Type | Glyphosate Acid Equivalent Content | | |
|---|---|---|---|---|
| | | (ae wt %) | (g ae/L) | pH |
| G-4-2 | Choline hydroxide (Choline) | 40.7 | 517 | 7.2 |
| G-5-1 | Diglycolamine (DGA) | 38.0 | 517 | 7.1 |
| G-6-1 | Isopropylamine (IPA) | 42.4 | 513 | 7.3 |
| G-6-2 | Isopropylamine (IPA) | 45.9 | 555 | 7.2 |
| G-7-1 | Potassium (K) | 35.9 | 506 | 7.2 |
| G-7-2 | Potassium (K) | 37.5 | 542 | 7.3 |

Example 2

Preparation of Dicamba Salt Solutions 50-60 g dicamba technical were mixed with water and reacted with 1.05 or higher molar equivalent amount of amine aqueous solutions or potassium hydroxide aqueous solution to form a homogenous clear solution at ambient temperature. Water was added, if needed, to reach a concentration of dicamba given in Table 2.

TABLE 2

| Sample ID | Amine Type | Dicamba Acid Equivalent Content | | |
|---|---|---|---|---|
| | | (ae wt %) | (g ae/L) | pH |
| D-1-1 | Diglycolamine (DGA) | 41.5 | 512 | 8.0 |
| D-1-2 | Diglycolamine (DGA) | 43.9 | 542 | 7.8 |
| D-2-1 | Dimethylamine (DMA) | 45.8 | 546 | 7.2 |
| D-3-1 | Dimethylethanolamine (DMEA) | 42.6 | 517 | 7.1 |
| D-3-2 | Dimethylethanolamine (DMEA) | 44.9 | 538 | 8.0 |
| D-4-1 | Choline hydroxide (Choline) | 43.7 | 529 | 7.5 |
| D-5-1 | Monoethanolamine (EA) | 42.5 | 514 | 7.8 |
| D-5-2 | Monoethanolamine (EA) | 44.3 | 538 | 8.0 |
| D-6-1 | Isopropylamine (IPA) | 41.9 | 490 | 8.0 |
| D-7-1 | Potassium (K) | 41.9 | 536 | 10.8 |

Example 3

Preparation of Glyphosate and Dicamba Mixture Compositions

Compositions were prepared by mixing a glyphosate salt solution in Table 1 with a dicamba salt solution in Table 2 and water if needed. The examples illustrated in Table 3 show the storage stability of the prior art compositions containing glyphosate and dicamba IPA salts. The examples given in Table 4 demonstrate the invention.

TABLE 3

| Formulation ID | Glyphosate salt solution, (amine type) | Dicamba salt solution, (amine type) | Total active content (g ae/L) | Weight ratio of glyphosate/ dicamba | Storage stability * | |
|---|---|---|---|---|---|---|
| | | | | | Ambient | −10° C. |
| 1 | G-6, (IPA) | D-6, (IPA) | 480 | 3:1 | C | C |
| 2 | G-6, (IPA) | D-6, (IPA) | 480 | 1.5:1 | C | C |
| 3 | G-6, (IPA) | D-6, (IPA) | 480 | 1:1 | C | C |
| 4 | G-6, (IPA) | D-6, (IPA) | 290 | 3:1 | C | C |
| 5 | G-6, (IPA) | D-6, (IPA) | 279 | 1.5:1 | C | C |
| 6 | G-6, (IPA) | D-6, (IPA) | 272 | 1:1 | C | C |
| 7 | G-6, (IPA) | D-6, (IPA) | 283 | 3:1 | H | H |

TABLE 3-continued

| Formulation ID | Glyphosate salt solution, (amine type) | Dicamba salt solution, (amine type) | Total active content (g ae/L) | Weight ratio of glyphosate/ dicamba | Storage stability * Ambient | −10° C. |
|---|---|---|---|---|---|---|
| 8 | G-6, (IPA) | D-6, (IPA) | 272 | 1.5:1 | H | H |
| 9 | G-6, (IPA) | D-6, (IPA) | 256 | 1:1 | H | H |

* Storage stability: "C" indicates crystallization of either salt or water in the formulation after 3 days of storage at the given temperature. "H" indicates a homogenous aqueous solution in the formulation after at least 1 day of storage at the given temperature.

TABLE 4

| Formulation ID | Glyphosate salt solution, (amine or K type) | Dicamba salt solution, (amine type) | Total active content (g ae/L) | Weight ratio of glyphosate/ dicamba | Storage stability ** Ambient | −10° C. |
|---|---|---|---|---|---|---|
| 10 | G-1, (DMA) | D-1, (DGA) | 480 | 3:1 | ✓ | ✓ |
| 11 | G-1, (DMA) | D-1, (DGA) | 480 | 1.5:1 | ✓ | ✓ |
| 12 | G-1, (DMA) | D-1, (DGA) | 480 | 1:1 | ✓ | ✓ |
| 13 | G-1, (DMA) | D-2, (DMA) | 480 | 3:1 | ✓ | ✓ |
| 14 | G-1, (DMA) | D-2, (DMA) | 480 | 1.5:1 | ✓ | ✓ |
| 15 | G-1, (DMA) | D-2, (DMA) | 480 | 1:1 | ✓ | ✓ |
| 16 | G-1, (DMA) | D-3, (DMEA) | 480 | 3:1 | ✓ | ✓ |
| 17 | G-1, (DMA) | D-3, (DMEA) | 480 | 1.5:1 | ✓ | ✓ |
| 18 | G-1, (DMA) | D-3, (DMEA) | 480 | 1:1 | ✓ | ✓ |
| 19 | G-1, (DMA) | D-4, (Choline) | 480 | 3:1 | ✓ | ✓ |
| 20 | G-1, (DMA) | D-4, (Choline) | 480 | 1.5:1 | ✓ | ✓ |
| 21 | G-1, (DMA) | D-4, (Choline) | 480 | 1:1 | ✓ | ✓ |
| 22 | G-1, (DMA) | D-5, (EA) | 480 | 3:1 | ✓ | ✓ |
| 23 | G-1, (DMA) | D-5, (EA) | 480 | 1.5:1 | ✓ | ✓ |
| 24 | G-1, (DMA) | D-5, (EA) | 480 | 1:1 | ✓ | ✓ |
| 25 | G-2, (EA) | D-1, (DGA) | 480 | 3:1 | ✓ | ✓ |
| 26 | G-2, (EA) | D-1, (DGA) | 480 | 1.5:1 | ✓ | ✓ |
| 27 | G-2, (EA) | D-1, (DGA) | 480 | 1:1 | ✓ | ✓ |
| 28 | G-2, (EA) | D-2, (DMA) | 480 | 3:1 | ✓ | ✓ |
| 29 | G-2, (EA) | D-2, (DMA) | 480 | 1.5:1 | ✓ | ✓ |
| 30 | G-2, (EA) | D-2, (DMA) | 480 | 1:1 | ✓ | ✓ |
| 31 | G-2, (EA) | D-3, (DMEA) | 480 | 3:1 | ✓ | ✓ |
| 32 | G-2, (EA) | D-3, (DMEA) | 480 | 1.5:1 | ✓ | ✓ |
| 33 | G-2, (EA) | D-3, (DMEA) | 480 | 1:1 | ✓ | ✓ |
| 34 | G-2, (EA) | D-4, (Choline) | 480 | 3:1 | ✓ | ✓ |
| 35 | G-2, (EA) | D-4, (Choline) | 480 | 1.5:1 | ✓ | ✓ |
| 36 | G-2, (EA) | D-4, (Choline) | 480 | 1:1 | ✓ | ✓ |
| 37 | G-2, (EA) | D-5, (EA) | 480 | 3:1 | ✓ | ✓ |
| 38 | G-2, (EA) | D-5, (EA) | 480 | 1.5:1 | ✓ | ✓ |
| 39 | G-2, (EA) | D-5, (EA) | 480 | 1:1 | ✓ | ✓ |
| 40 | G-3, (DMEA) | D-1, (DGA) | 480 | 3:1 | ✓ | ✓ |
| 41 | G-3, (DMEA) | D-1, (DGA) | 480 | 1.5:1 | ✓ | ✓ |
| 42 | G-3, (DMEA) | D-1, (DGA) | 480 | 1:1 | ✓ | ✓ |
| 43 | G-3, (DMEA) | D-2, (DMA) | 480 | 3:1 | ✓ | ✓ |
| 44 | G-3, (DMEA) | D-2, (DMA) | 480 | 1.5:1 | ✓ | ✓ |
| 45 | G-3, (DMEA) | D-2, (DMA) | 480 | 1:1 | ✓ | ✓ |
| 46 | G-3, (DMEA) | D-3, (DMEA) | 480 | 3:1 | ✓ | ✓ |
| 47 | G-3, (DMEA) | D-3, (DMEA) | 480 | 1.5:1 | ✓ | ✓ |
| 48 | G-3, (DMEA) | D-3, (DMEA) | 480 | 1:1 | ✓ | ✓ |
| 49 | G-3, (DMEA) | D-4, (Choline) | 480 | 3:1 | ✓ | ✓ |
| 50 | G-3, (DMEA) | D-4, (Choline) | 480 | 1.5:1 | ✓ | ✓ |
| 51 | G-3, (DMEA) | D-4, (Choline) | 480 | 1:1 | ✓ | ✓ |
| 52 | G-3, (DMEA) | D-5, (EA) | 480 | 3:1 | ✓ | ✓ |
| 53 | G-3, (DMEA) | D-5, (EA) | 480 | 1.5:1 | ✓ | ✓ |
| 54 | G-3, (DMEA) | D-5, (EA) | 480 | 1:1 | ✓ | ✓ |
| 55 | G-4, (Choline) | D-1, (DGA) | 480 | 3:1 | ✓ | ✓ |
| 56 | G-4, (Choline) | D-1, (DGA) | 480 | 1.5:1 | ✓ | ✓ |
| 57 | G-4, (Choline) | D-1, (DGA) | 480 | 1:1 | ✓ | ✓ |
| 58 | G-4, (Choline) | D-2, (DMA) | 480 | 3:1 | ✓ | ✓ |
| 59 | G-4, (Choline) | D-2, (DMA) | 480 | 1.5:1 | ✓ | ✓ |
| 60 | G-4, (Choline) | D-2, (DMA) | 480 | 1:1 | ✓ | ✓ |
| 61 | G-4, (Choline) | D-3, (DMEA) | 480 | 3:1 | ✓ | ✓ |
| 62 | G-4, (Choline) | D-3, (DMEA) | 480 | 1.5:1 | ✓ | ✓ |
| 63 | G-4, (Choline) | D-3, (DMEA) | 480 | 1:1 | ✓ | ✓ |
| 64 | G-4, (Choline) | D-4, (Choline) | 480 | 3:1 | ✓ | ✓ |
| 65 | G-4, (Choline) | D-4, (Choline) | 480 | 1.5:1 | ✓ | ✓ |
| 66 | G-4, (Choline) | D-4, (Choline) | 480 | 1:1 | ✓ | ✓ |
| 67 | G-4, (Choline) | D-5, (EA) | 480 | 3:1 | ✓ | ✓ |

TABLE 4-continued

| Formulation ID | Glyphosate salt solution, (amine or K type) | Dicamba salt solution, (amine type) | Total active content (g ae/L) | Weight ratio of glyphosate/ dicamba | Storage stability ** Ambient | Storage stability ** −10° C. |
|---|---|---|---|---|---|---|
| 68 | G-4, (Choline) | D-5, (EA) | 480 | 1.5:1 | ✓ | ✓ |
| 69 | G-4, (Choline) | D-5, (EA) | 480 | 1:1 | ✓ | ✓ |
| 70 | G-5, (DGA) | D-1, (DGA) | 480 | 3:1 | ✓ | ✓ |
| 71 | G-5, (DGA) | D-1, (DGA) | 480 | 1.5:1 | ✓ | ✓ |
| 72 | G-5, (DGA) | D-1, (DGA) | 480 | 1:1 | ✓ | ✓ |
| 73 | G-5, (DGA) | D-2, (DMA) | 480 | 3:1 | ✓ | ✓ |
| 74 | G-5, (DGA) | D-2, (DMA) | 480 | 1.5:1 | ✓ | ✓ |
| 75 | G-5, (DGA) | D-2, (DMA) | 480 | 1:1 | ✓ | ✓ |
| 76 | G-5, (DGA) | D-3, (DMEA) | 480 | 3:1 | ✓ | ✓ |
| 77 | G-5, (DGA) | D-3, (DMEA) | 480 | 3:1 | ✓ | ✓ |
| 78 | G-5, (DGA) | D-3, (DMEA) | 480 | 1.5:1 | ✓ | ✓ |
| 79 | G-5, (DGA) | D-4, (Choline) | 480 | 3:1 | ✓ | ✓ |
| 80 | G-5, (DGA) | D-4, (Choline) | 480 | 1.5:1 | ✓ | ✓ |
| 81 | G-5, (DGA) | D-4, (Choline) | 480 | 1:1 | ✓ | ✓ |
| 82 | G-5, (DGA) | D-5, (EA) | 480 | 3:1 | ✓ | ✓ |
| 83 | G-5, (DGA) | D-5, (EA) | 480 | 1.5:1 | ✓ | ✓ |
| 84 | G-5, (DGA) | D-5, (EA) | 480 | 1:1 | ✓ | ✓ |
| 85 | G-7, (K) | D-1, (DGA) | 449 | 3:1 | ✓ | ✓ |
| 86 | G-7, (K) | D-1, (DGA) | 462 | 1.5:1 | ✓ | ✓ |
| 87 | G-7, (K) | D-2, (DMA) | 436 | 3:1 | ✓ | ✓ |
| 88 | G-7, (K) | D-2, (DMA) | 449 | 1.5:1 | ✓ | ✓ |
| 89 | G-7, (K) | D-3, (DMEA) | 425 | 3:1 | ✓ | ✓ |
| 90 | G-7, (K) | D-3, (DMEA) | 436 | 1.5:1 | ✓ | ✓ |
| 91 | G-7, (K) | D-4, (Choline) | 384 | 3:1 | ✓ | ✓ |
| 92 | G-7, (K) | D-4, (Choline) | 384 | 1.5:1 | ✓ | ✓ |
| 93 | G-7, (K) | D-5, (EA) | 480 | 3:1 | ✓ | ✓ |
| 94 | G-7, (K) | D-5, (EA) | 480 | 1.5:1 | ✓ | ✓ |
| 95 | G-7, (K) | D-5, (EA) | 480 | 3:1 | ✓ | ✓ |
| 96 | G-7, (K) | D-7, (K) | 520 | 1.5:1 | ✓ | ✓ |
| 97 | G-7, (K) | D-7, (K) | 520 | 3:1 | ✓ | ✓ |
| 98 | G-6, (IPA) | D-7, (K) | 384 | 1.5:1 | ✓ | ✓ |
| 99 | G-6, (IPA) | D-7, (K) | 375 | 3:1 | ✓ | ✓ |
| 100 | G-4, (Choline) | D-7, (K) | 440 | 1.5:1 | ✓ | ✓ |
| 101 | G-4, (Choline) | D-7, (K) | 436 | 3:1 | ✓ | ✓ |
| 102 | G-5, (DGA) | D-7, (K) | 480 | 1.5:1 | ✓ | ✓ |
| 103 | G-5, (DGA) | D-7, (K) | 480 | 3:1 | ✓ | ✓ |
| 104 | G-2, (EA) | D-7, (K) | 480 | 1.5:1 | ✓ | ✓ |
| 105 | G-2, (EA) | D-7, (K) | 449 | 3:1 | ✓ | ✓ |
| 106 | G-3, (DMEA) | D-7, (K) | 453 | 1.5:1 | ✓ | ✓ |
| 107 | G-3, (DMEA) | D-7, (K) | 429 | 3:1 | ✓ | ✓ |
| 108 | G-1, (DMA) | D-7, (K) | 420 | 1.5:1 | ✓ | ✓ |
| 109 | G-1, (DMA) | D-7, (K) | 393 | 3:1 | ✓ | ✓ |

** Storage stability: "✓" indicates a clear, homogeneous, free-flowing fluid without any phase separation or crystallization after at least 3 days of storage at the given temperature.

Example 4

Glyphosate and Dicamba Compositions with Improved Cold Temperature Storage Stability by Using Co-Solvent Composition (with formulation ID of 10 in Table 4) was prepared by mixing 4.35 g glyphosate dimethylamine salt solution (G-1-1 in Table 1) with 1.37 g dicamba diglycolamine salt solution (D-1-2 in Table 2, containing 25 wt % diethylene glycol as cosolvent) at a weight ratio of 3:1. The total active content is 480 g ae/L. The final composition contains 6 wt % diethylene glycol. It formed a clear, homogeneous solution after preparation at ambient temperature. It remained stable and homogeneous at 54° C., 0° C., −10° C., and −20° C. over 15 days, without phase separation or crystal formation. The compositions were clear, homogeneous, free-flowing liquids.

What is claimed is:

1. A homogeneous, stable, high-strength aqueous herbicidal concentrate composition comprising:
   (a) water,
   (b) a glyphosate potassium or amine salt, and
   (c) a dicamba potassium or amine salt,
in which (i) the glyphosate salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (ii) the dicamba salt is potassium or a secondary, tertiary or quaternary alkylamine or a primary, secondary, tertiary or quaternary alkanolamine, alkylalkanolamine or alkoxyalkanolamine salt, wherein the alkyl and alkanol groups are saturated and contain from $C_1$-$C_4$ carbon atoms individually, (iii) the composition contains a total active ingredient loading of at least 300 g ae/L of the glyphosate potassium or amine salt and the dicamba potassium or amine salt, (iv) the acid equivalent weight ratio of the glyphosate potassium or amine salt to the dicamba potassium or amine salt is from about 1:1 to about 3:1, and (v) the pH is from about 6.0 to about 8.0.

2. A composition of claim 1 which contains a total active ingredient loading of greater than about 450 grams of acid equivalent of the glyphosate potassium or amine salt and the dicamba potassium or amine salt.

3. A composition of claim 1 in which the acid equivalent weight ratio of the glyphosate potassium or amine salt to the dicamba potassium or amine salt is about 1.5:1 to about 3:1.

4. A composition of claim 1 in which the pH is from about 6.5 to about 7.5.

5. A composition of claim 1 in which the glyphosate salt is potassium or a monoethanolamine, dimethylethanolamine, dimethylamine, diglycolamine or choline salt.

6. A composition of claim 1 in which the dicamba salt is potassium or a dimethylamine, monoethanolamine, dimethylethanolamine, choline or diglycolamine salt.

7. A method of controlling undesirable vegetation in crops that are resistant or tolerant to both glyphosate and dicamba which comprises applying to the undesirable vegetation and the crops that are resistant or tolerant to both glyphosate and dicamba a water-diluted composition of claim 1.

8. A composition of claim 1 in which the glyphosate salt is a monoethanolamine, dimethylethanolamine, diglycolamine, or choline salt.

9. A composition of claim 1 in which the dicamba salt is a monoethanolamine, dimethylethanolamine, diglycolamine, or choline salt.

10. A composition of claim 1 wherein the glyphosate salt is a dimethylamine salt and the dicamba salt is a diglycolamine, dimethylamine, dimethylethanolamine, choline, monoethanolamine, or potassium salt.

11. A composition of claim 1 wherein the glyphosate salt is a monoethanolamine salt and the dicamba salt is a diglycolamine, dimethylamine, dimethylethanolamine, choline, or monoethanolamine salt.

12. A composition of claim 1 wherein the glyphosate salt is a dimethylethanolamine salt and the dicamba salt is a diglycolamine, dimethylamine, dimethylethanolamine, choline, monoethanolamine, or potassium salt.

13. A composition of claim 1 wherein the glyphosate salt is a diglycolamine salt and the dicamba salt is a diglycolamine, dimethylamine, dimethylethanolamine, choline, monoethanolamine, or potassium salt.

14. A composition of claim 1 wherein the glyphosate salt is a choline salt and the dicamba salt is a diglycolamine, dimethylamine, dimethylethanolamine, choline, monoethanolamine, or potassium salt.

15. A composition of claim 1 wherein the glyphosate salt is a potassium salt and the dicamba salt is a diglycolamine, dimethylamine, dimethylethanolamine, choline, or monoethanolamine salt.

16. A composition of claim 1 wherein the dicamba salt is a dimethylamine salt and the glyphosate salt is a diglycolamine, dimethylamine, dimethylethanolamine, choline, monoethanolamine, or potassium salt.

17. A composition of claim 1 wherein the dicamba salt is a monoethanol amine salt and the glyphosate salt is a diglycolamine, dimethylamine, dimethylethanolamine, choline, monoethanolamine, or potassium salt.

18. A composition of claim 1 wherein the dicamba salt is a dimethylethanolamine salt and the glyphosate salt is a diglycolamine, dimethylamine, dimethylethanolamine, choline, monoethanolamine, or potassium salt.

19. A composition of claim 1 wherein the dicamba salt is a diglycolamine salt and the glyphosate salt is a diglycolamine, dimethylamine, dimethylethanolamine, choline, monoethanolamine, or potassium salt.

20. A composition of claim 1 wherein the dicamba salt is a choline salt and the glyphosate salt is a diglycolamine, dimethylamine, dimethylethanolamine, choline, monoethanolamine, or potassium salt.

21. A composition of claim 1 wherein the dicamba salt is a potassium salt and the glyphosate salt is a diglycolamine, dimethylamine, dimethylethanolamine, choline, or monoethanolamine salt.

* * * * *